(12) United States Patent
Negiz et al.

(10) Patent No.: US 7,393,989 B2
(45) Date of Patent: Jul. 1, 2008

(54) SHAPED CATALYSTS FOR TRANSALKYLATION OF AROMATICS FOR ENHANCED XYLENES PRODUCTION

(75) Inventors: Antoine Negiz, Wilmette, IL (US); Edwin P. Boldingh, Arlington Heights, IL (US); Gregory J. Gajda, Mount Prospect, IL (US); Sergey V. Gurevich, San Mateo, CA (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 11/678,857

(22) Filed: Feb. 26, 2007

(65) Prior Publication Data

US 2007/0142688 A1 Jun. 21, 2007

Related U.S. Application Data

(62) Division of application No. 10/925,604, filed on Aug. 24, 2004, now Pat. No. 7,202,189, which is a division of application No. 10/141,294, filed on May 7, 2002, now Pat. No. 6,815,570.

(51) Int. Cl.
 *C07C 6/10* (2006.01)
(52) U.S. Cl. .................................................. 585/475
(58) Field of Classification Search .................. 585/475
 See application file for complete search history.

(56) References Cited

U.S. PATENT DOCUMENTS

| | | | |
|---|---|---|---|
| 3,308,069 A | 3/1967 | Wadlinger et al. | 252/455 |
| 3,832,449 A | 8/1974 | Rosinski et al. | 423/328 |
| 4,159,282 A | 6/1979 | Olson et al. | 585/481 |
| 4,163,018 A | 7/1979 | Tada et al. | 260/429.9 |
| 4,185,040 A | 1/1980 | Ward et al. | 585/467 |
| 4,278,565 A | 7/1981 | Chen et al. | 252/455 Z |
| 4,835,131 A | 5/1989 | DeJong | 502/255 |
| 4,857,666 A | 8/1989 | Barger et al. | 585/323 |
| 4,876,228 A | 10/1989 | Chang et al. | 502/71 |
| 5,028,406 A | 7/1991 | Occelli | 423/328 |
| 5,043,509 A | 8/1991 | Imai et al. | 585/466 |
| 5,200,382 A | 4/1993 | Cody et al. | 502/204 |
| 5,232,578 A | 8/1993 | Gillespie | 208/59 |
| 5,723,710 A | 3/1998 | Gajda et al. | 585/467 |
| 5,763,720 A | 6/1998 | Buchanan et al. | 585/475 |
| 5,942,651 A | 8/1999 | Beech, Jr. et al. | 585/475 |
| 5,952,536 A | 9/1999 | Nacamuli et al. | 585/475 |
| 6,060,417 A | 5/2000 | Kato et al. | 502/66 |

(Continued)

OTHER PUBLICATIONS

W.M. Meier et al., *Zeolites*, 17:A1-A6, 1996, pp. 76-77 and 108-109.

(Continued)

*Primary Examiner*—Thuan Dinh Dang
(74) *Attorney, Agent, or Firm*—Mary Ann Maas

(57) ABSTRACT

A catalyst, a process for using the catalyst whereby the catalyst effectively transalkylates $C_7$, $C_9$, and $C_{10}$ aromatics to $C_8$ aromatics are disclosed. The catalyst comprises a support such as mordenite plus a metal component. The catalyst provides an enhanced life and activity for carrying out the transalkylation reactions at relatively low temperatures. This is achieved by reducing the maximum particle diameter of cylindrical pellets to 1/32 inch (0.08 cm) or a trilobe to 1/16 inch (0.16 cm).

20 Claims, 1 Drawing Sheet

U.S. PATENT DOCUMENTS

| | | |
|---|---|---|
| 6,268,305 B1 | 7/2001 | Butler et al. .................. 502/77 |
| 6,500,997 B2 | 12/2002 | Cheng et al. ................ 585/475 |
| 6,815,570 B1 | 11/2004 | Negiz et al. ................. 585/475 |
| 6,888,037 B2 | 5/2005 | Dandekar et al. ........... 585/467 |
| 6,897,346 B1 | 5/2005 | Merrill et al. ............... 585/323 |
| 2003/0097030 A1 | 5/2003 | Arnoldy ..................... 568/895 |
| 2003/0173256 A1 | 9/2003 | Fujikawa et al. ............ 208/217 |

OTHER PUBLICATIONS

Chen-Ho Tung et al., *Pure and Applied Chemistry*, vol. 72, No. 12, pp. 2289-2298, 2000.

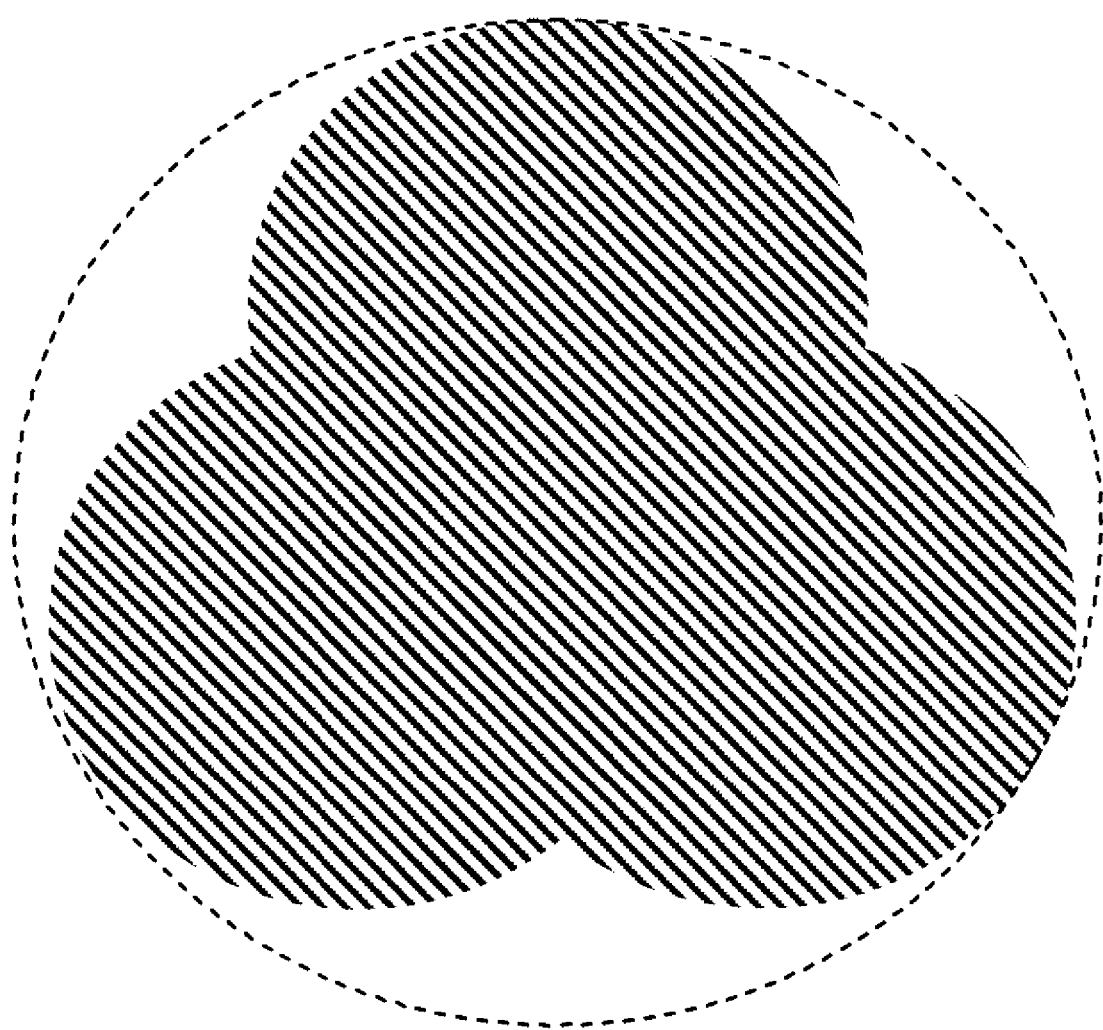

SHAPED CATALYSTS FOR TRANSALKYLATION OF AROMATICS FOR ENHANCED XYLENES PRODUCTION

CROSS-REFERENCE TO RELATED APPLICATIONS

This application is a Division of copending application Ser. No. 10/925,604 filed Aug. 24, 2004, which in turn is a Division of application Ser. No. 10/141,294 filed May 7, 2002, now U.S. Pat. No. 6,815,570, the contents of which are hereby incorporated by reference in their entirety.

FIELD OF THE INVENTION

This invention relates to catalytic hydrocarbon conversion, and more specifically to the use of a catalyst for transalkylation of $C_7$, $C_9$, and $C_{10}$ aromatics to $C_8$ aromatics at relatively low temperatures. Said catalyst comprises a suitable solid-acid support such as mordenite, beta, MFI, silica-alumina or a combination thereof with or without a suitable metal element promoter such as platinum, germanium, or rhenium. The catalyst is extruded into either a trilobe with a maximum effective diameter of 1/16 inch (0.16 cm) or cylindrical pellets with a maximum diameter of 1/32 inch (0.08 cm).

BACKGROUND OF THE INVENTION

The xylenes, para-xylene, meta-xylene and ortho-xylene, are important intermediates which find wide and varied application in chemical syntheses. Para-xylene upon oxidation yields terephthalic acid, which is used in the manufacture of synthetic textile fibers and resins. Meta-xylene is used in the manufacture of plasticizers, azo dyes, wood preservers, etc. Ortho-xylene is feedstock for phthalic anhydride production.

Xylene isomers from catalytic reforming or other sources generally do not match demand proportions as chemical intermediates, and further comprise ethylbenzene, which is difficult to separate or to convert. Para-xylene in particular is a major chemical intermediate with rapidly growing demand, but amounts to only 20-25% of a typical $C_8$ aromatics stream.

Ethylbenzene generally is present in xylene mixtures and is occasionally recovered for styrene production, but usually is considered a less-desirable component of $C_8$ aromatics.

Among the aromatic hydrocarbons, the overall importance of the xylenes rivals that of benzene as a feedstock for industrial chemicals. Neither the xylenes nor benzene are produced from petroleum by the reforming of naphtha in sufficient volume to meet demand, and conversion of other hydrocarbons is necessary to increase the yield of xylenes and benzene. Often toluene ($C_7$) is dealkylated to produce benzene ($C_6$) or selectively disproportionated to yield benzene and $C_8$ aromatics from which the individual xylene isomers are recovered.

A current objective of many aromatics complexes is to increase the yield of xylenes and to de-emphasize benzene production. Demand is growing faster for xylene derivatives than for benzene derivatives. Refinery modifications are being effected to reduce the benzene content of gasoline in industrialized countries, which will increase the supply of benzene available to meet demand. Benzene produced from disproportionation processes often is not sufficiently pure to be competitive in the market. A higher yield of xylenes at the expense of benzene thus is a favorable objective, and processes to transalkylate $C_9$ aromatics and toluene have been commercialized to obtain high xylene yields.

U.S. Pat. No. 4,857,666 (Barger et al.) discloses a transalkylation process over mordenite and suggests modifying the mordenite by steam deactivation or incorporating a metal modifier into the catalyst.

U.S. Pat. No. 5,043,509 (Imai et al.) discloses a process for conversion of organic compounds with a phosphoric catalyst consisting of a shaped extrudate with a specific maximum ratio of length to diameter representing the ratio of exterior surface area to catalyst volume. Shaped catalysts have also been described in U.S. Pat. No. 4,185,040 (Ward et al.) for use in an olefin alkylation catalyst comprising Y zeolite.

U.S. Pat. No. 5,763,720 (Buchanan et al.), discloses a transalkylation process for conversion of $C_9$+ over a catalyst containing zeolites illustrated in an extensive list including amorphous silica-alumina, MCM-22, ZSM-12, and zeolite beta, where the catalyst further contains a Group VIII metal such as platinum.

U.S. Pat. No. 5,942,651 (Beech, Jr. et al.) discloses a transalkylation process in the presence of two zeolite containing catalysts. The first zeolite is selected from the group consisting of MCM-22, PSH-3, SSZ-25, ZSM-12, and zeolite beta. The second zeolite contains ZSM-5, and is used to reduce the level of saturate co-boilers in making a higher purity benzene product.

U.S. Pat. No. 5,952,536 (Nacamuli et al.) discloses a transalkylation process using a catalyst comprising a zeolite selected from the group consisting of SSZ-26, A1-SSZ-33, CIT-1, SSZ-35, and SSZ-44. The catalyst also comprises a mild hydrogenation metal such as nickel or palladium, and can be used to convert aromatics with at least one alkyl group including benzene.

U.S. Pat. No. 6,060,417 (Kato et al.), discloses a transalkylation process using a catalyst based on mordenite with a particular zeolitic particle diameter and having a feedstream limited to a specific amount of ethyl containing heavy aromatics. Said catalyst contains nickel or rhenium metal.

Thus, many types of supports and elements have been disclosed for use as catalysts in processes to transalkylate various types of aromatics into xylenes. However, applicants have found that the specific size of the catalyst used for these processes provides a surprising benefit when reduced to a smaller than expected size, or shaped to increase the exterior surface area per gram of catalyst. Both of these size limitations effectively increase the diffusion of $C_6$ to $C_{10}$ aromatics and enhance aromatic mass transfer rates to the surface.

SUMMARY OF THE INVENTION

A principal object of the present invention is to provide a process for the transalkylation of alkylaromatic hydrocarbons. More specifically, the process of the present invention is directed to converting aromatic hydrocarbons with improved yields of desired xylene isomers over a size-limited catalyst. This invention is based on the discovery that specific size limitations increase the exterior surface area per gram of catalyst and demonstrate improved activity in transalkylating toluene with $C_9$+ aromatics.

Accordingly, a broad embodiment of the present invention is a catalyst for transalkylation of $C_7$, $C_9$, and $C_{10}$ aromatics to $C_8$ aromatics having a trilobe shape with a maximum effective diameter of 1/16 inch (0.16 cm). The catalyst is composed of a support, which can be selected from the group consisting of mordenite, beta, MFI, silica-alumina and mixtures thereof. The catalyst is also composed of an optional element deposited on the support selected from the group consisting of platinum, tin, lead, indium, germanium, rhenium, or any combination of these elements. The catalyst also can contain a binder, which is preferably alumina. The preferred support is mordenite.

In an alternate embodiment, the catalyst has a cylindrical shape with a maximum diameter of 1/32 inch (0.08 cm). Preferably the cylindrical shape can be characterized by a maximum average aspect ratio of 3.

The invention also encompasses a process for transalkylation of aromatics comprising contacting a feedstream comprising $C_7$, $C_9$, and $C_{10}$ aromatics with a catalyst at transalkylation conditions to produce a product stream comprising $C_8$ aromatics. Transalkylation conditions comprise a temperature from about 200° C. to about 540° C., a pressure from about 100 kPa to about 6 MPa absolute, and a space velocity from about 0.1 to about 20 hr$^{-1}$. A preferred temperature range is from about 300° C. to about 500° C.

These, as well as other objects and embodiments will become evident from the following detailed description of the invention.

BRIEF DESCRIPTION OF THE FIGURE

The FIGURE shows a trilobe shaped transalkylation catalyst of the present invention with a maximum effective diameter of 1/6" (0.16 cm).

DETAILED DESCRIPTION OF THE INVENTION

The feedstream to the present process comprises alkylaromatic hydrocarbons of the general formula $C_6H_{(6-n)}R_n$, where n is an integer from 0 to 5 and R is $CH_3$, $C_2H_5$, $C_3H_7$, or $C_4H_9$, in any combination. Suitable alkylaromatic hydrocarbons include, for example but without so limiting the invention, benzene, toluene, ortho-xylene, meta-xylene, para-xylene, ethylbenzene, ethyltoluenes, propylbenzenes, tetramethylbenzenes, ethyl-dimethylbenzenes, diethylbenzenes, methylpropylbenzenes, ethylpropylbenzenes, triethylbenzenes, di-isopropylbenzenes, and mixtures thereof.

The feedstream preferably comprises benzene, toluene, and $C_9$ aromatics and suitably is derived from one or a variety of sources. Feedstock may be produced synthetically, for example, from naphtha by catalytic reforming or by pyrolysis followed by hydrotreating to yield an aromatics-rich product. The feedstock may be derived from such product with suitable purity by extraction of aromatic hydrocarbons from a mixture of aromatic and nonaromatic hydrocarbons and fractionation of the extract. For instance, aromatics may be recovered from a reformate. The reformate may be produced by any of the processes known in the art, with a process based on platinum containing L-zeolite being especially preferred for lower carbon number aromatic production. The aromatics then may be recovered from the reformate with the use of a selective solvent, such as one of the sulfolane type, in a liquid-liquid extraction zone. The recovered aromatics may then be separated into streams having the desired carbon number range by fractionation. The feedstock should contain no more than about 10 mass-% non-aromatics; the content of benzene and $C_8$ aromatics is principally an economic decision relating to the efficiency of conversion to toluene from these aromatics. When the severity of reforming or pyrolysis is sufficiently high, extraction may be unnecessary and fractionation may be sufficient to prepare the feedstock. Benzene may also be recovered from the product of transalkylation.

A preferred component of the feedstock is a heavy-aromatics stream comprising $C_9$ aromatics, thereby effecting transalkylation of toluene and $C_9$ aromatics to yield additional xylenes. Benzene may also be transalkylated to yield additional toluene. Indan may be present in the heavy-aromatics stream although it is not a desirable component to effect high yields of $C_8$ aromatics product. $C_{10}$+ aromatics also may be present, preferably in an amount of 30% or less of the feed. The heavy-aromatics stream preferably comprises at least about 90 mass-% aromatics, and may be derived from the same or different known refinery and petrochemical processes as the benzene and toluene feedstock and/or may be recycled from the separation of the product from transalkylation.

The feedstock is preferably transalkylated in the vapor phase and in the presence of hydrogen. If transalkylated in the liquid phase, then the presence of hydrogen is optional. If present, free hydrogen is associated with the feedstock and recycled hydrocarbons in an amount of from about 0.1 moles per mole of alkylaromatics up to 10 moles per mole of alkylaromatic. This ratio of hydrogen to alkylaromatic is also referred to as hydrogen to hydrocarbon ratio. The transalkylation reaction preferably yields a product having an increased xylene content and also comprises toluene.

The feed to a transalkylation reaction zone usually first is heated by indirect heat exchange against the effluent of the reaction zone and then is heated to reaction temperature by exchange with a warmer stream, steam or a furnace. The feed then is passed through a reaction zone, which may comprise one or more individual reactors. The use of a single reaction vessel having a fixed cylindrical bed of catalyst is preferred, but other reaction configurations utilizing moving beds of catalyst or radial-flow reactors may be employed if desired. Passage of the combined feed through the reaction zone effects the production of an effluent stream comprising unconverted feed and product hydrocarbons. This effluent is normally cooled by indirect heat exchange against the stream entering the reaction zone and then further cooled through the use of air or cooling water. The effluent may be passed into a stripping column in which substantially all $C_5$ and lighter hydrocarbons present in the effluent are concentrated into an overhead stream and removed from the process. An aromatics-rich stream is recovered as net stripper bottoms which is referred to herein as the transalkylation effluent.

To effect a transalkylation reaction, the present invention incorporates a transalkylation catalyst in at least one zone, but no limitation is intended in regard to a specific catalyst other than size and shape. Conditions employed in the transalkylation zone normally include a temperature of from about 200° C. to about 540° C. The transalkylation zone is operated at moderately elevated pressures broadly ranging from about 100 kPa to about 6 MPa absolute. The transalkylation reaction can be effected over a wide range of space velocities, with higher space velocities effecting a higher ratio of para-xylene at the expense of conversion. Weighted hourly space velocity (WHSV) generally is in the range of from about 0.1 to about 20 hr$^{-1}$.

The transalkylation effluent is separated into a light recycle stream, a mixed $C_8$ aromatics product and a heavy-aromatics stream. The mixed $C_8$ aromatics product can be sent for recovery of para-xylene and other valuable isomers. The light recycle stream may be diverted to other uses such as to benzene and toluene recovery, but alternatively is recycled partially to the transalkylation zone. The heavy recycle stream contains substantially all of the $C_9$ and heavier aromatics and may be partially or totally recycled to the transalkylation reaction zone.

One skilled in the art is familiar with several types of transalkylation catalysts that may be suitably sized and shaped for use in the present invention. For example, in U.S. Pat. No. 3,849,340, which is herein incorporated by reference, a catalytic composite is described comprising a mordenite component having a $SiO_2/Al_2O_3$ mole ratio of at least 40:1 prepared by acid extracting $Al_2O_3$ from mordenite prepared with an initial $SiO_2/Al_2O_3$ mole ratio of about 12:1 to about 30:1 and a metal component selected from copper, silver and zirconium. Friedel-Crafts metal halides such as aluminum chloride have been employed with good results and are suitable for use in the present process. Hydrogen halides, boron halides, Group I-A metal halides, iron group metal halides, etc., have been found suitable. Refractory inorganic oxides, combined with the above-mentioned and other known catalytic materials, have been found useful in transalkylation operations. For instance, silica-alumina is described in U.S. Pat. No. 5,763,720, which is incorporated herein by reference. Crystalline aluminosilicates have also been employed in the art as transalkylation catalysts. ZSM-12 is more particularly described in U.S. Pat. No. 3,832,449, which is incorporated herein by reference. Zeolite beta is more particularly described in U.S. Pat. No. Re. 28,341 (of original U.S. Pat. No. 3,308,069) which is incorporated herein by reference. A favored form of zeolite beta is described in U.S. Pat. No. 5,723,710, which is incorporated herein by reference. The preparation of MFI topology zeolite is also well known in the art. In one method, the zeolite is prepared by crystallizing a mixture containing an alumina source, a silica source, an alkali metal source, water and an alkyl ammonium compound or its precursor. Further descriptions are in U.S. Pat. No. 4,159,282, U.S. Pat. No. 4,163,018, and U.S. Pat. No. 4,278,565, all of which are incorporated herein by reference.

A refractory binder or matrix is optionally utilized to facilitate fabrication of the catalyst, provide strength and reduce fabrication costs. The binder should be uniform in composition and relatively refractory to the conditions used in the process. Suitable binders include inorganic oxides such as one or more of alumina, magnesia, zirconia, chromia, titania, boria, thoria, phosphate, zinc oxide and silica. Alumina is a preferred binder.

The catalyst also contains an optional metal component. One preferred metal component is a Group VIII (IUPAC 8-10) metal, preferably a platinum-group metal. Alternatively a preferred metal component is rhenium. Of the preferred platinum group, i.e., platinum, palladium, rhodium, ruthenium, osmium and iridium, platinum is especially preferred. This component may exist within the final catalytic composite as a compound such as an oxide, sulfide, halide, or oxyhalide, in chemical combination with one or more of the other ingredients of the composite, or, preferably, as an elemental metal. This component may be present in the final catalyst composite in any amount which is catalytically effective, generally comprising about 0.01 to about 2 mass-% of the final catalyst calculated on an elemental basis. The platinum-group metal component may be incorporated into the catalyst in any suitable manner such as coprecipitation or cogellation with the carrier material, ion exchange or impregnation. Impregnation using water-soluble compounds of the metal is preferred. Typical platinum-group compounds which may be employed are chloroplatinic acid, ammonium chloroplatinate, bromoplatinic acid, platinum dichloride, platinum tetrachloride hydrate, tetraamine platinum chloride, tetraamine platinum nitrate, platinum dichlorocarbonyl dichloride, dinitrodiaminoplatinum, palladium chloride, palladium chloride dihydrate, palladium nitrate, etc. Chloroplatinic acid is preferred as a source of the especially preferred platinum component. Moreover, when the metal component is rhenium, typical rhenium compounds which may be employed include ammonium perrhenate, sodium perrhenate, potassium perrhenate, potassium rhenium oxychloride, potassium hexachlororhenate (IV), rhenium chloride, rhenium heptoxide, and the like compounds. The utilization of an aqueous solution of perrhenic acid is highly preferred in the impregnation of the rhenium component. Rhenium may also be used in conjunction with a platinum-group metal.

The catalyst may optionally contain a modifier component. Preferred metal components of the catalyst include, for example, tin, germanium, lead, indium, and mixtures thereof. Catalytically effective amounts of such metal modifiers may be incorporated into the catalyst by any means known in the art. A preferred amount is a range of about 0.01 to about 2.0 mass-% on an elemental basis.

One preferred shape of the catalyst of the present invention is a cylinder with a maximum diameter of 1/32 inch (0.08 cm). Such cylinders can be formed using extrusion methods known to the art. They can be characterized with an aspect ratio of height divided by diameter, such that a preferred maximum aspect ratio is 3.

Another preferred shape of the catalyst is one having a trilobal or three-leaf clover type of cross section. This has been illustrated in the FIGURE. The maximum diameter of the trilobe shape is defined by circumscribing effectively a circle around the entire cloverleaf shape. Then using the diameter of that effective circle, the maximum diameter of the trilobe shaped catalyst is 1/16 in. (0.16 cm).

EXAMPLES

The following examples are presented only to illustrate certain specific embodiments of the invention, and should not be construed to limit the scope of the invention as set forth in the claims. There are many possible other variations, as those of ordinary skill in the art will recognize, within the scope of the invention.

Example One

Samples of catalysts comprising mordenite were prepared for comparative pilot-plant testing by the forming process called extrusion. Typically, 2500 g of a powder blend of 25% alumina (commercially available under the trade names Catapal™ B and/or Versal™ 250) and 75% mordenite (commercially available under the trade name Zeolyst™ CBV-10A, which has been ammonium exchanged to remove sodium) was added to a mixer. A solution was prepared using 10 g nitric acid (67.5% $HNO_3$) with 220 g deionized water and the solution was stirred. The solution was added to the powder blend in the mixer, and mulled to make a dough suitable for extrusion. The dough was extruded through a die plate to form extrudate particles. The extrudate particles were dried on a belt calciner operating with a first zone at 340° C. for about 45 minutes and a second zone at 570° C. for about 90 minutes.

Based on three different die plates, three differently shaped extrudate catalyst particles were prepared. Catalyst A was a 1/16 inch (0.16 cm) cylinder, which was prepared to match the state of the art. Catalyst B was a 1/16 inch (0.16 cm) trilobe, as shown in the FIGURE, which was prepared to demonstrate an embodiment of the invention. Catalyst C was a 1/32 inch (0.08 cm) cylinder, which was prepared to demonstrate another embodiment of the invention.

Example Two

Catalysts A, B, and C were tested for aromatics transalkylation ability in a pilot plant using three different feed blends to demonstrate effectiveness of $C_9+$ conversion as compared to toluene conversion. The test consisted of loading a vertical reactor with catalyst and contacting the feed at 400 psig (2860 kPa abs) under a specified space velocity (WHSV) and hydrogen to hydrocarbon ratio ($H_2$/HC). Activity was determined by targeting an overall conversion of feedstock based on a reactor temperature measurement. Thus, a lower temperature indicates a catalyst with better activity.

These three feeds compared toluene against feeds containing $C_9+$. The $C_9+$ component contained about 70 wt-% $C_9$ aromatics and about 30 wt-% $C_{10}$ aromatics. The results from this test are summarized in the table below indicating equivalent start of run activity at 35 wt-% overall conversion for a feed blend consisting of 15 wt-% $C_7$. Also included are results indicating start of run activity at 50 wt-% overall conversion for feed blends consisting of 50 wt-% $C_7$ and 100 Wt-% $C_7$.

TABLE

| Feed Blends | Catalyst A | Catalyst B | Catalyst C |
|---|---|---|---|
| {15 wt-% $C_7$ and 85 wt-% $C_9+$}[1] | 454° C. | 417° C. | 415° C. (trial 1) 427° C. (trial 2) |
| {50 wt-% $C_7$ and 50 wt-% $C_9+$}[2] | 417° C. | 405° C. | 406° C. |
| {100 wt-% $C_7$}[3] | 397° C. | 394° C. | 395° C. |

[1] Activity test at 35% conversion, 4.0 hr$^{-1}$ WHSV, and 4:1 $H_2$/HC
[2] Activity test at 50% conversion, 1.8 hr$^{-1}$ WHSV, and 6:1 $H_2$/HC
[3] Activity test at 50% conversion, 4.0 hr$^{-1}$ WHSV, and 6:1 $H_2$/HC The data indicated that catalysts B and C had better activity than the state of the art catalyst A, and a difference greater than 5° C. was generally considered to be significant between catalysts. Moreover, the data indicated that the activity difference increased as the presence of the heavier aromatic blend component, as exemplified by $C_9+$, was increased.

What is claimed is:

1. A process for the transalkylation of aromatics comprising contacting, at transalkylation conditions, a feedstream comprising $C_7$, $C_9$, and $C_{10}$ aromatics with a catalyst to produce a product stream comprising $C_8$ aromatics, wherein the catalyst comprises a component selected from the group consisting of a mixture of mordenite and MFI topology zeolite and a mixture of mordenite, MFI topology zeolite and silica-alumina; an optional element deposited on the component selected from the group consisting of platinum-group metal, tin, lead, indium, germanium, rhenium, nickel, iron, cobalt or a combination thereof; and the catalyst having a trilobe shape with a maximum effective diameter of 1/16 inch (0.16 cm).

2. The process of claim 1 wherein the transalkylation conditions comprise a temperature from about 200° C. to about 540° C., a pressure from about 100 kPa to about 6 MPa absolute, and a space velocity from about 0.1 to about 20 hr$^{-1}$.

3. The process of claim 1 wherein the catalyst further comprises a binder.

4. The process of claim 3 wherein the binder is alumina.

5. The process of claim 1 wherein the component is a mixture of mordenite and MFI topology zeolite.

6. A process for the transalkylation of aromatics comprising contacting, at transalkylation conditions, a feedstream comprising $C_7$, $C_9$, and $C_{10}$ aromatics with a catalyst to produce a product stream comprising $C_8$ aromatics, wherein the catalyst comprises a component selected from the group consisting of a mixture of mordenite and MFI topology zeolite and a mixture of mordenite, MFI topology zeolite and silica-alumina; an optional element deposited on the component selected from the group consisting of platinum-group metal, tin, lead, indium, germanium, rhenium, nickel, iron, cobalt or a combination thereof; the catalyst having a cylindrical shape with a maximum diameter of 1/32 inch (0.08 cm).

7. The process of claim 6 wherein the transalkylation conditions comprise a temperature from about 200° C. to about 540° C., a pressure from about 100 kPa to about 6 MPa absolute, and a space velocity from about 0.1 to about 20 hr$^{-1}$.

8. The process of claim 6 wherein the cylindrical shape is characterized by a maximum average aspect ratio of 3.

9. The process of claim 6 wherein the catalyst further comprises a binder.

10. The process of claim 9 wherein the binder is alumina.

11. The process of claim 6 wherein the component is a mixture of mordenite and MFI topology zeolite.

12. A process for the transalkylation of aromatics comprising contacting, at transalkylation conditions, a feedstream comprising $C_7$, $C_9$, and $C_{10}$ aromatics with a catalyst to produce a product stream comprising $C_8$ aromatics, wherein the catalyst comprises a component selected from the group consisting of a mixture of mordenite and MFI topology zeolite and a mixture of mordenite, MFI topology zeolite and silica-alumina; an element deposited on the component selected from the group consisting of platinum-group metal, tin, lead, indium, germanium, rhenium, nickel, iron, cobalt or a combination thereof; the catalyst having a trilobe shape with a maximum effective diameter of 1/16 inch (0.16 cm).

13. The process of claim 12 wherein the catalyst further comprises a binder.

14. The process of claim 13 wherein the binder is alumina.

15. The process of claim 12 wherein the component is a mixture of mordenite and MFI topology zeolite.

16. A process for the transalkylation of aromatics comprising contacting, at transalkylation conditions, a feedstream comprising $C_7$, $C_9$, and $C_{10}$ aromatics with a catalyst to produce a product stream comprising $C_8$ aromatics, wherein the catalyst comprises a component selected from the group consisting of a mixture of mordenite and MFI topology zeolite and a mixture of mordenite, MFI topology zeolite and silica-alumina; an element deposited on the component selected from the group consisting of platinum-group metal, tin, lead, indium, germanium, rhenium, nickel, iron, cobalt or a combination thereof; the catalyst having a cylindrical shape with a maximum diameter of 1/32 inch (0.08 cm).

17. The process of claim 16 wherein the cylindrical shape is characterized by a maximum average aspect ratio of 3.

18. The process of claim 16 wherein the catalyst further comprises a binder.

19. The process of claim 18 wherein the binder is alumina.

20. The process of claim 16 wherein the component is a mixture of mordenite and MFI topology zeolite.

* * * * *